US00PP21506P2

(12) United States Plant Patent
Oudshoorn

(10) Patent No.: US PP21,506 P2
(45) Date of Patent: Nov. 16, 2010

(54) ***SEDUM* PLANT NAMED 'RAINBOW XENOX'**

(50) Latin Name: *Hylotelephium spectabile*
Varietal Denomination: Rainbow Xenox

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/459,834

(22) Filed: Jul. 8, 2009

(51) Int. Cl.
*A01H 5/00* (2006.01)

(52) U.S. Cl. ..... Plt./479

(58) Field of Classification Search ..... Plt./479
See application file for complete search history.

*Primary Examiner*—June Hwu
(74) *Attorney, Agent, or Firm*—C. A. Whealy

(57) ABSTRACT

A new and distinct cultivar of *Sedum* plant named 'Rainbow Xenox', characterized by its upright plant habit; sturdy and strong branches; attractive greyed purple-colored flowers; and good garden performance.

2 Drawing Sheets

Botanical designation: *Hylotelephium spectabile.*
Cultivar denomination: 'RAINBOW XENOX'.

BACKGROUND OF THE INVENTION

The present invention relates to a new and distinct cultivar of *Sedum* plant, botanically known as *Hylotelephium spectabile* and hereinafter referred to by the name 'Rainbow Xenox'.

The new *Sedum* plant is a product of a planned breeding program conducted by the Inventor in Rijpwetering, The Netherlands. The objective of the breeding program is to create new strong and healthy *Sedum* cultivars with numerous attractive flowers.

The new *Sedum* plant originated from an open-pollination during the summer of 2004 in Rijpwetering, The Netherlands, of an unnamed selection of *Hylotelephium spectabile,* not patented, as the female, or seed, parent with an unknown selection of *Hylotelephium spectabile,* not patented, as the male, or pollen, parent. The new *Sedum* was discovered and selected by the Inventor as a single flowering plant within the progeny of the stated open-pollination in a controlled greenhouse environment in Rijpwetering, The Netherlands during the summer of 2005.

Asexual reproduction of the new *Sedum* plant by vegetative cuttings in a controlled environment in Rijpwetering, The Netherlands since the summer of 2005, has shown that the unique features of this new *Sedum* plant are stable and reproduced true to type in successive generations.

SUMMARY OF THE INVENTION

Plants of the new *Sedum* have not been observed under all possible environmental conditions. The phenotype may vary somewhat with variations in environment such as temperature and light intensity without, however, any variance in genotype.

The following traits have been repeatedly observed and are determined to be the unique characteristics of 'Rainbow Xenox'. These characteristics in combination distinguish 'Rainbow Xenox' as a new and distinct cultivar of *Sedum:*

1. Upright plant habit.
2. Sturdy and strong branches.

3. Attractive greyed purple-colored flowers.
4. Good garden performance.

Plants of the new *Sedum* differ from plants of the female parent selection primarily in flower color as plants of the female parent selection have yellow green-colored flowers.

Plants of the new *Sedum* can be compared to plants of *Sedum telephium* 'Sunkissed', disclosed in U.S. Plant Pat. No. 16,927. Plants of the new *Sedum* and 'Sunkissed' differ primarily in flower color as plants of 'Sunkissed' have yellow-colored flowers.

BRIEF DESCRIPTION OF THE PHOTOGRAPHS

The accompanying colored photographs illustrate the overall appearance of the new *Sedum* plant, showing the colors as true as it is reasonably possible to obtain in colored reproductions of this type. Colors in the photographs may differ slightly from the color values cited in the detailed botanical description which accurately describe the colors of the new *Sedum* plant.

The photograph on the first sheet comprises a side perspective view of a typical flowering plant of 'Rainbow Xenox' grown in a container.

The photograph at the top of the second sheet is a close-up view of typical inflorescences of 'Rainbow Xenox'.

The photograph at the bottom of the second sheet is a close-up view of a typical leaf of 'Rainbow Xenox'.

DETAILED BOTANICAL DESCRIPTION

The aforementioned photographs and following observations, measurements and values describe plants grown in Rijpwetering, The Netherlands, under commercial practice during the autumn in an outdoor nursery with day temperatures ranging from 12° C. to 25° C. and night temperatures ranging from 2° C. to 14° C. Plants used in the photographs and description were two years old. In the following description, color references are made to The Royal Horticultural Society Colour Chart, 2007 Edition, except where general terms of ordinary dictionary significance are used.

Botanical classification: *Hylotelephium spectabile* 'Rainbow Xenox'.

Parentage:

*Female, or seed, parent.*—Unnamed selection of *Hylotelephium spectabile,* not patented.

*Male, or pollen, parent.*—Unknown selection of *Hylotelephium spectabile,* not patented.

Propagation:

*Type.*—By vegetative cuttings.

*Time to initiate roots.*—About 15 to 20 days at 18° C.

*Time to produce a rooted young plant.*—About two months at 16° C. to 22° C.

*Root description.*—Moderately thick and moderately fleshy; white to medium brown in color.

*Rooting habit.*—Moderately freely branching; moderately dense.

Plant description:

*Plant form/habit.*—Herbaceous perennial; upright plant habit; inverted triangle; moderately vigorous growth habit; basally branching habit with about four basal branches developing per plant.

*Plant height.*—About 17.4 cm.

*Plant width* (*spread*).—About 17.6 cm.

*Lateral branches.*—Length: About 11.7 cm. Diameter: About 5 mm. Internode length: About 3.9 cm. Strength: Strong. Texture: Smooth, glabrous. Color: Close to 144C tinged with close to 177B to 177C.

Foliage description:

*Arrangement.*—Opposite, simple; sessile.

*Length.*—About 5.9 cm.

*Width.*—About 3.9 cm.

*Shape.*—Ovate.

*Apex.*—Broadly acute.

*Base.*—Truncate.

*Margin.*—Irregularly and shallowly dentate.

*Texture, upper and lower surfaces.*—Smooth, glabrous; succulent.

*Venation pattern.*—Pinnate.

*Color.*—Developing leaves, upper surface: Between N137B and 147A; towards the base, tinged with close to 184A. Developing leaves, lower surface: Close to 148B. Fully expanded leaves, upper surface: Close to N137A; venation, close to 144B to 144C. Fully expanded leaves, lower surface: Close to 191A; venation, close to 144B to 144C.

Flower description:

*Flower type/habit.*—Small rotate flowers arranged in terminal compound cymes; flowers face upright to slightly outward; freely flowering habit with about 1,500 flower buds and flowers developing per plant.

*Fragrance.*—None detected.

*Natural flowering season.*—Continuously flowering from August to late October in The Netherlands.

*Postproduction longevity.*—Flowers last about two weeks on the plant; flowers persistent.

*Flower buds.*—Height: About 3.5 mm. Diameter: About 1.5 mm. Shape: Ovate. Color: Close to 186C to 186D; towards the base, close to 194A to 194B.

*Inflorescence height.*—About 7.3 cm.

*Inflorescence diameter.*—About 6.1 cm.

*Flower diameter.*—About 4 mm.

*Flower depth.*—About 4 mm.

*Petals.*—Quantity per flower: Typically five in a single whorl; petals fused at the base. Length: About 3 mm. Lobe width: About 1 mm. Shape: Ovate. Apex: Acute. Margin: Entire. Texture, upper and lower surfaces: Smooth, glabrous. Color: When opening, upper and lower surfaces: Close to 159A to 159B. Fully opened, upper and lower surfaces: Close to 159A to 159B, flushed with close to 186D.

*Sepals.*—Quantity per flower: Typically five in a single whorl, fused at the base. Length: About 2 mm. Width: About 1 mm. Shape: Ovate. Apex: Acute. Margin: Entire. Texture, upper and lower surfaces: Smooth, glabrous. Color: When opening, upper and lower surfaces: Close to 194A to 194B. Fully opened, upper and lower surfaces: Between 194A to 194B and 148B.

*Peduncles.*—Length: About 6.3 cm. Diameter: About 3 mm. Angle: Erect to about 35° from vertical. Strength: Moderately strong. Texture: Smooth, glabrous. Color: Close to 144C tinged with close to 177B to 177C.

*Pedicels.*—Length: About 2 mm. Diameter: About 0.7 mm. Angle: Erect to about 40° from vertical. Strength: Moderately strong. Texture: Smooth, glabrous. Color: Close to 144A to 144B.

*Reproductive organs.*—Stamens: None observed. Pistils: Quantity per flower: Five. Pistil length: About 3 mm. Stigma shape: Pointed. Stigma color: Close to 64A. Style length: About 2 mm. Style color: Close to 186D; towards the apex, close to 64B; color becoming closer to 185A with development. Ovary color: Close to 155B to 155C; color becoming closer to 185A with development.

*Seed/fruit.*—Seed and fruit development have not been observed.

Disease/pest resistance: Plants of the new *Sedum* have not been noted to be resistant to pathogens and pests common to *Sedum.*

Garden performance: Plants of the new *Sedum* have been observed to have good garden performance and tolerate rain and wind. Plants of the new *Sedum* tolerate high temperatures of about 35° C. and are winter hardy to USDA Hardiness Zone 5.

It is claimed:

1. A new and distinct *Sedum* plant named 'Rainbow Xenox' as illustrated and described.

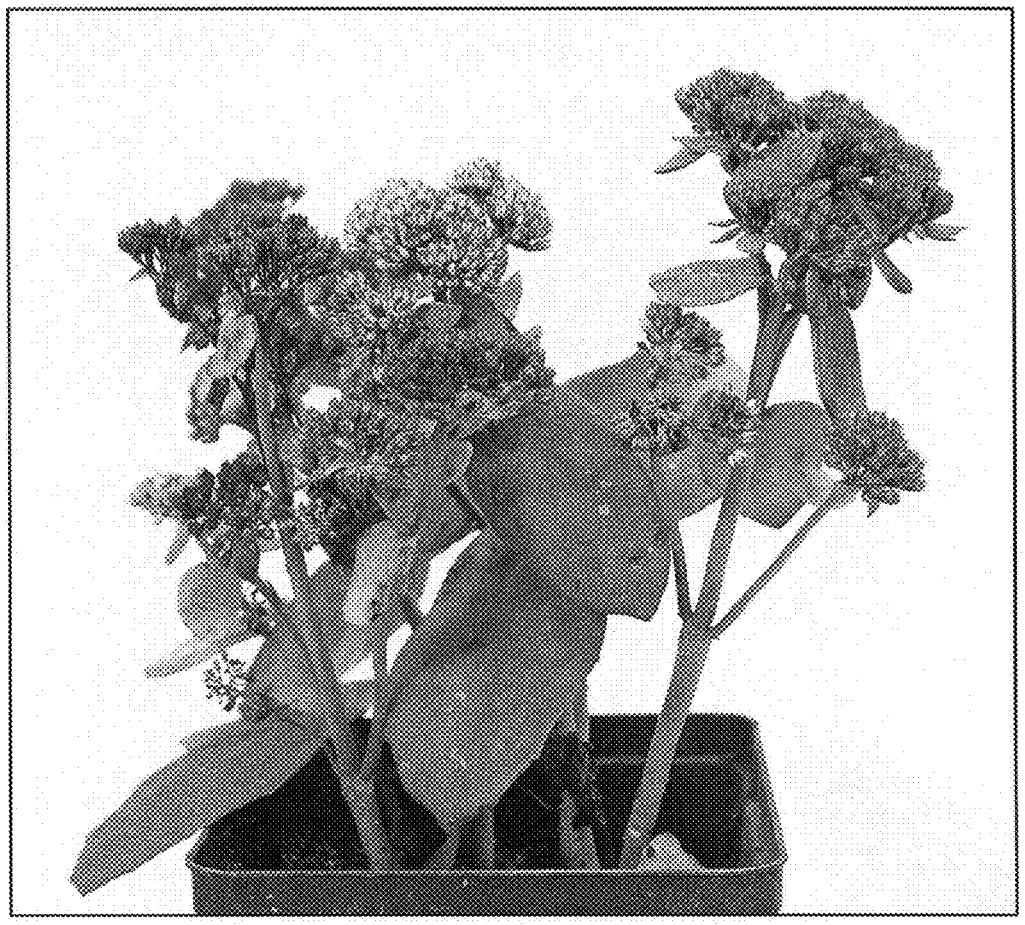

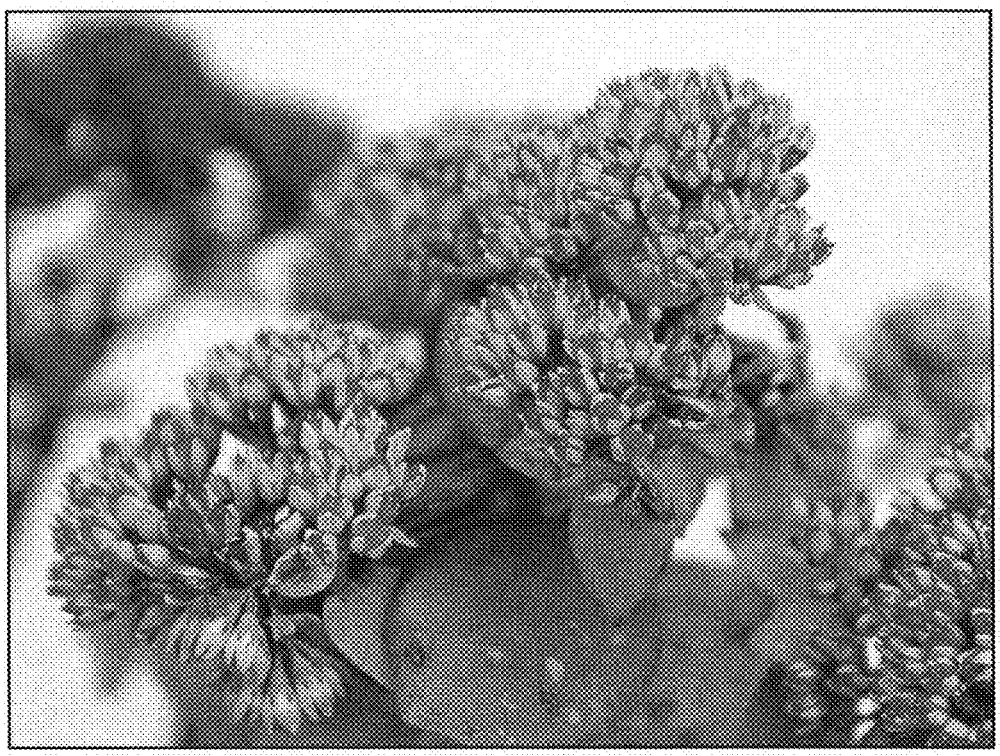
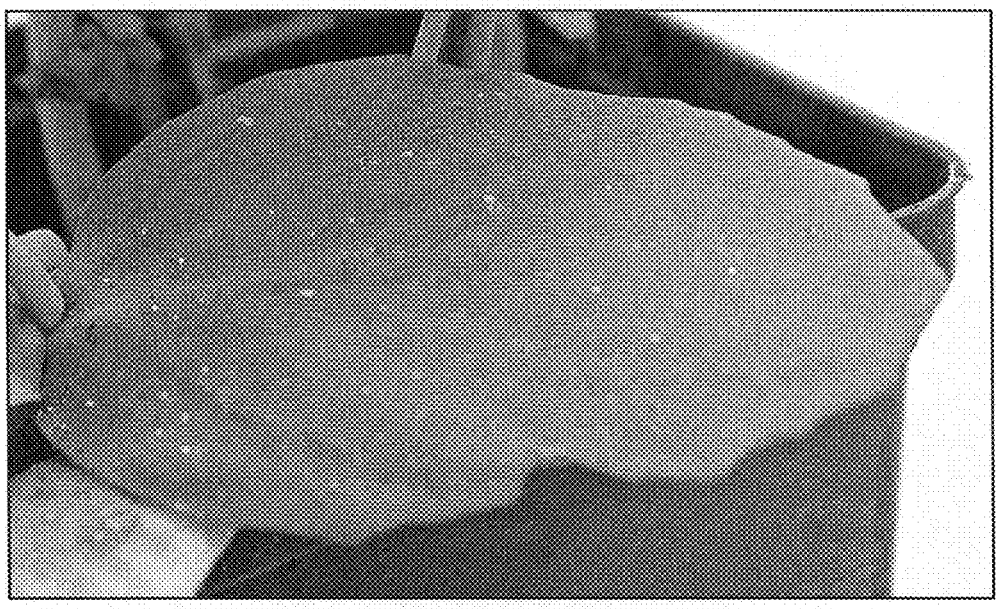

* * * * *